US008565851B2

(12) United States Patent
Lau et al.

(10) Patent No.: US 8,565,851 B2
(45) Date of Patent: Oct. 22, 2013

(54) MONO-PHASIC ACTION POTENTIAL ELECTROGRAM RECORDING CATHETER, AND METHOD

(75) Inventors: Michael Lau, Fremont, CA (US); Randell Werneth, San Diego, CA (US); Timothy J. Corvi, Carlsbad, CA (US); Sumita Bhola, Irvine, CA (US); Mark T. Stewart, Lino Lakes, MN (US); Michel Haïssaguerre, Bordeaux-Pessac (FR); Meleze Hocini, Pessac (FR)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 612 days.

(21) Appl. No.: 12/533,903

(22) Filed: Jul. 31, 2009

(65) Prior Publication Data

US 2011/0028966 A1 Feb. 3, 2011

Related U.S. Application Data

(63) Continuation of application No. 12/511,707, filed on Jul. 29, 2009, now Pat. No. 8,280,477.

(51) Int. Cl.
*A61B 5/042* (2006.01)
*A61B 18/14* (2006.01)
*A61N 1/05* (2006.01)

(52) U.S. Cl.
USPC .............................. 600/374; 606/41; 607/122

(58) Field of Classification Search
USPC ......................................................... 600/374
See application file for complete search history.

(56) References Cited

U.S. PATENT DOCUMENTS

| | | | |
|---|---|---|---|
| 4,630,611 A | 12/1986 | King | |
| 4,848,352 A | 7/1989 | Pohndorf et al. | |
| 4,979,510 A | 12/1990 | Franz et al. | |
| 5,306,292 A | 4/1994 | Lindegren | |
| 5,398,683 A | 3/1995 | Edwards et al. | |
| 5,423,878 A | 6/1995 | Franz | |
| 5,680,860 A * | 10/1997 | Imran | 600/374 |
| 5,692,926 A | 12/1997 | Jarl | |
| 5,836,875 A | 11/1998 | Webster, Jr. | |
| 6,068,629 A * | 5/2000 | Haissaguerre et al. | 606/41 |
| 6,134,463 A | 10/2000 | Wittkampf et al. | |
| 6,152,882 A | 11/2000 | Prutchi | |
| 6,162,219 A | 12/2000 | Nilsson et al. | |
| 6,405,067 B1 | 6/2002 | Mest et al. | |

(Continued)

FOREIGN PATENT DOCUMENTS

DE 69716940 T2 7/2003

*Primary Examiner* — Lee S Cohen

(74) *Attorney, Agent, or Firm* — Christopher & Weisberg, P.A.

(57) ABSTRACT

Catheters and methods for obtaining monophasic action potential ("MAP") electrograms include a flexible catheter body defining a longitudinal axis, and a distal assembly affixed to the catheter body distal end defining a distal tip. The distal assembly has at least three MAP recording electrodes, and at least one reference electrode for determining reference potential. The recording electrodes are each positioned a radial distance from the longitudinal axis in at least three different radial directions, defining a recording geometry substantially having radial symmetry. The reference electrode is a longitudinal distance from the recording geometry. Optional features include a steerable catheter shaft, one or more radio-frequency ablation electrodes, and a dedicated pacing electrode. Different possible embodiments include a dome housing having the recording electrodes in a fixed spatial arrangement, and a distal loop assembly having an array of electrodes on at least three flexible loop elements.

4 Claims, 11 Drawing Sheets

(56) References Cited

U.S. PATENT DOCUMENTS

| | | |
|---|---|---|
| 6,615,483 B2 | 9/2003 | Lindegren |
| 7,826,881 B1 * | 11/2010 | Beatty et al. .................. 600/374 |
| 2002/0151889 A1 | 10/2002 | Swanson et al. |
| 2005/0043765 A1 | 2/2005 | Williams et al. |
| 2006/0111700 A1 * | 5/2006 | Kunis et al. .................... 606/41 |
| 2007/0083194 A1 | 4/2007 | Kunis et al. |
| 2007/0083195 A1 | 4/2007 | Werneth et al. |
| 2008/0243214 A1 | 10/2008 | Koblish |

* cited by examiner

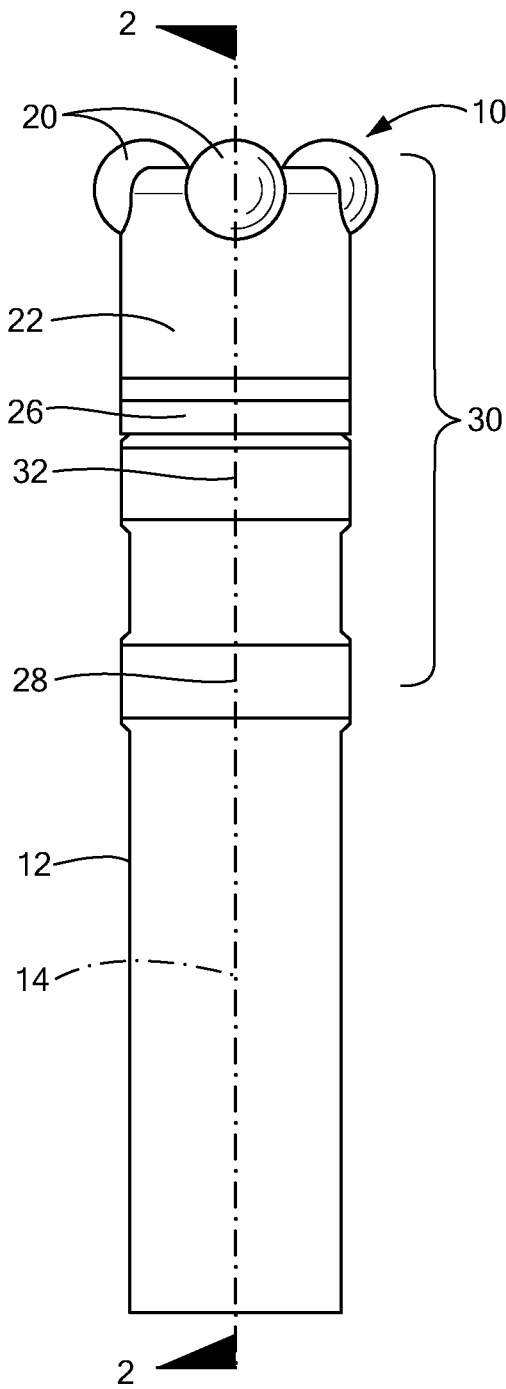
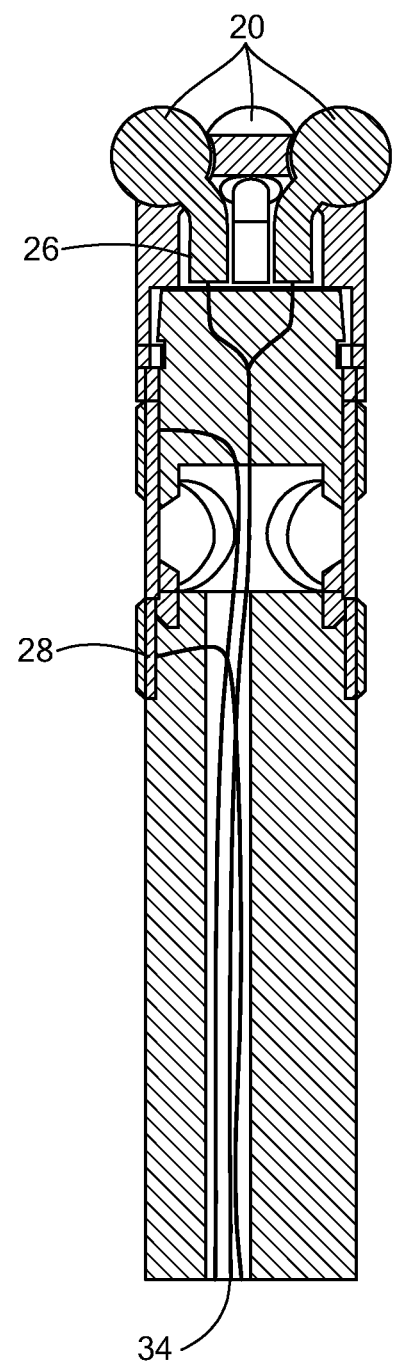
*FIG. 1*
*FIG. 2*

MONO-PHASIC ACTION POTENTIAL ELECTROGRAM RECORDING CATHETER, AND METHOD

CROSS-REFERENCE TO RELATED APPLICATION

This application is a continuation of patent application Ser. No. 12/511,707, filed Jul. 29, 2009, now U.S. Pat. No. 8,280,477, entitled MONO-PHASIC ACTION POTENTIAL ELECTROGRAM RECORDING CATHETER, AND METHOD, the entirety of which is incorporated herein by reference.

STATEMENT REGARDING FEDERALLY SPONSORED RESEARCH OR DEVELOPMENT

Not applicable.

FIELD OF THE INVENTION

The present invention relates generally to medical devices, and more particularly to catheters and methods for obtaining monophasic action potential electrograms.

BACKGROUND OF THE INVENTION

Normal sinus rhythm of the heart begins with an electrical impulse generated by the sinus node that propagates across the right and left atria (the two small upper chambers of the heart) to the atrioventricular node. Atrial contraction leads to pumping blood into the ventricles in synchronization with the electrical pulse.

The term "atrial fibrillation" is a type of cardiac arrhythmia, or irregular heartbeat, in which the atria fail to contract effectively. During atrial fibrillation, disorganized electrical conduction in the atria causes rapid uncoordinated contractions, resulting in sub-optimal pumping of blood into the ventricle. The atrioventricular node may receive sporadic electrical impulses from many locations throughout the atria, instead of only from the sinus node. This electrical confusion may overwhelm the atrioventricular node, producing an irregular and rapid heartbeat. Consequently, blood may pool in the atria and increase a risk for blood clots.

While there are numerous variations of atrial fibrillation with different causes, they all involve irregularities in the transmission of electrical impulses through the heart. As a result, the heart does not pump the blood properly, and it may pool and clot. If a blood clot forms and moves to an artery in the brain, atrial fibrillation can lead to stroke.

The major risk factors for atrial fibrillation include age, coronary artery disease, rheumatic heart disease, hypertension, diabetes, and thyrotoxicosis. Atrial fibrillation affects 7% of the population over 65 years of age, and is also associated with increased risks of congestive heart failure and cardiomyopathy, which warrant medical attention and treatment. Atrial fibrillation is the most common sustained heart rhythm disorder and increases the risk for heart disease and stroke, both leading causes of death in the United States.

Diagnosis and treatment of arrhythmias and atrial fibrillation may involve mapping or otherwise identifying and characterizing the electrical activity of the relevant anatomy, such as the cardiac tissue of the atria. Some tissues, such as those in the heart, have cells with a measurable internal voltage difference that may be useful in locating and mapping electrical signals. In particular, contact with positive pressure produces a monophasic action potential signal, which may be used to map proper and improper electrically functioning areas.

After mapping, tissue ablation may be used in various medical procedures to treat patients, such as to stop improper electrical propagation through the tissue in patients with an arrhythmia. Various ablation techniques have been proposed to treat atrial fibrillation.

SUMMARY OF THE INVENTION

The present invention advantageously provides catheters and methods for treating a patient by obtaining monophasic action potential ("MAP") electrograms, in the identification and treatment of electrical tissue disorders. The catheters include a flexible catheter body, and a distal assembly defining a distal tip. The distal assembly has at least two MAP recording electrodes, and at least one reference electrode for determining reference potential.

The recording electrodes are each positioned a radial distance from the longitudinal axis in at least two different radial directions, defining a recording geometry having substantial radial symmetry. The reference electrode is positioned a longitudinal distance from the recording geometry. A wire is connected to each recording electrode and to the reference electrode, for transmitting individual signals to the catheter body proximal end. The catheters and methods of the present invention facilitate good contact of at least one recording electrode with tissue and thus improve signal fidelity.

A more complete understanding of the present invention, and its associated advantages and features, will be more readily understood by reference to the following description and claims, when considered in conjunction with the accompanying drawings.

BRIEF DESCRIPTION OF THE DRAWINGS

In this description, reference will be made to the attached drawings:

FIG. 1 is a partial side elevation view of a catheter for recording monophasic action potential electrograms;

FIG. 2 is a partial longitudinal cross-section view along the line 2-2 of FIG. 1;

DETAILED DESCRIPTION OF THE INVENTION

Figure 3:
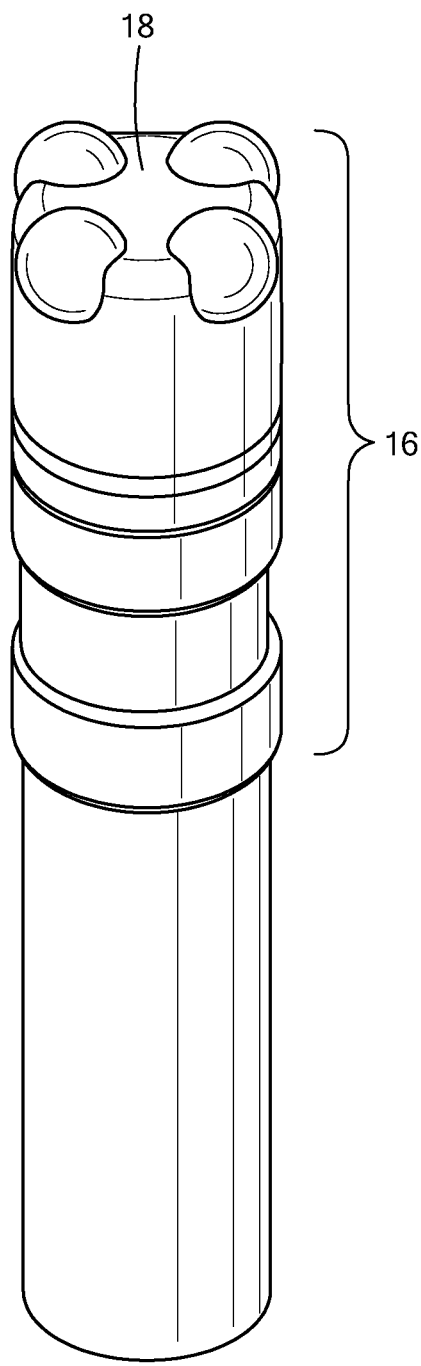
FIG. 3 is a partial external perspective view of the catheter of FIG. 1.
Figure 4:
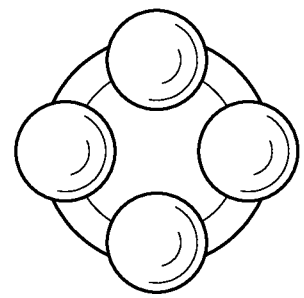
FIG. 4 is an end view of the catheter of FIG. 1.
Figure 5:
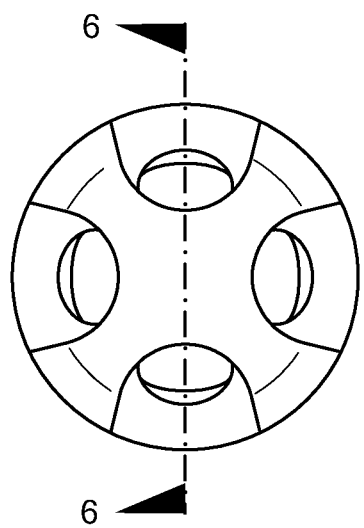
FIG. 5 is an end view of a dome housing of the catheter of FIG. 1.
Figure 6:
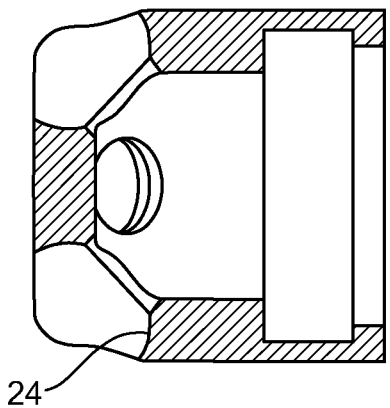
FIG. 6 is a longitudinal cross-section view along the line 6-6 of FIG. 5.
Figure 7:
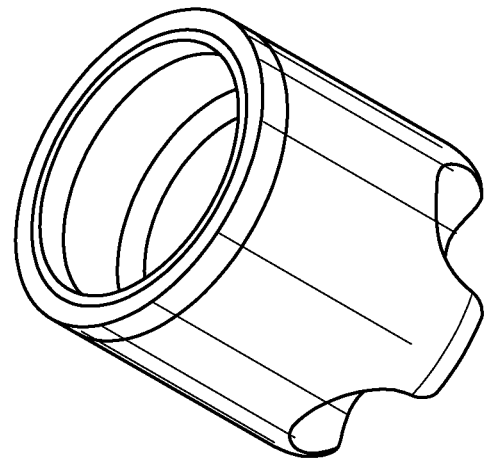
FIGS. 7-8 are external perspective views of the dome housing of FIG. 5.
Figure 8:
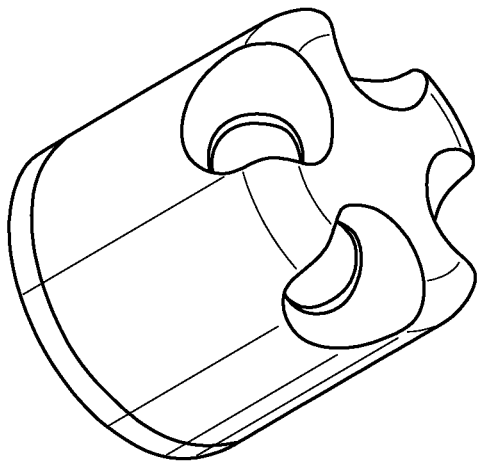

Referring to the drawings, an embodiment of the present invention provides a medical device for treating patients by obtaining monophasic action potential ("MAP") electrograms, which may be in the form of a catheter generally designated at reference numeral 10. The illustrated catheter 10 of course depicts only one of many different possible catheter designs that are within the scope of the present invention. For clarity and convenience, the present detailed description will only describe a few embodiments.

As shown in FIGS. 1-8, catheter 10 has a flexible catheter body 12 with proximal and distal ends, and defines a longitudinal axis 14. A distal assembly 16 may be affixed to the distal end of the catheter body 12 which defines a distal tip 18. The distal assembly 16 may for example include four MAP electrogram recording electrodes 20; each positioned a radial distance from the longitudinal axis 14 in different radial directions. The recording electrodes 20 define a recording geometry, which substantially has radial symmetry around the longitudinal axis. In the embodiment depicted in FIGS. 1-9, the recording geometry is a plane, perpendicular to the longitudinal axis. Specifically, FIGS. 1-9 depict four recording electrodes 20, each positioned at ninety degrees relative to the adjacent recording electrodes 20 around a circumference of the recording geometry.

Each recording electrode 20 may have a spherical recording surface, with a relatively small outer diameter. For example, recording electrodes 20 may have outer diameters of about one-half to two millimeters, and in one embodiment the recording electrodes 20 have a diameter of one millimeter.

Catheters according to the present invention may also include a radio-frequency ("RF") ablation electrode for ablating tissue to treat a patient.

The distal assembly 16 may also include a dome housing 22 having at least two sockets for receiving the recording electrodes 20 in a fixed spatial arrangement. Specifically in the illustrated embodiment of FIGS. 1-9, there are four sockets 24, and an electrically insulating material 26 is positioned between each recording electrode 20 and corresponding socket 24 in the dome housing 22. Accordingly, in this embodiment the dome housing 22 is made of an electrically conductive material that may be selected from the group consisting of silver, silver chloride, platinum, iridium, gold, stainless steel, aluminum, and alloys and combinations thereof, and may serve as an RF electrode capable of radiofrequency ablation.

A reference electrode 28 for determining reference potential may be included on the catheter shaft, positioned a certain longitudinal distance 30 from the recording geometry. Thus, the reference electrode 28 is a similar distance from each recording electrode 20. The electrical potential measured between recording electrodes 20 and the reference electrode 28 may be displayed or otherwise presented on a display to the physician for use in treating the patient. These signals may of course be displayed individually, or in the aggregate as one representation.

Figure 9:
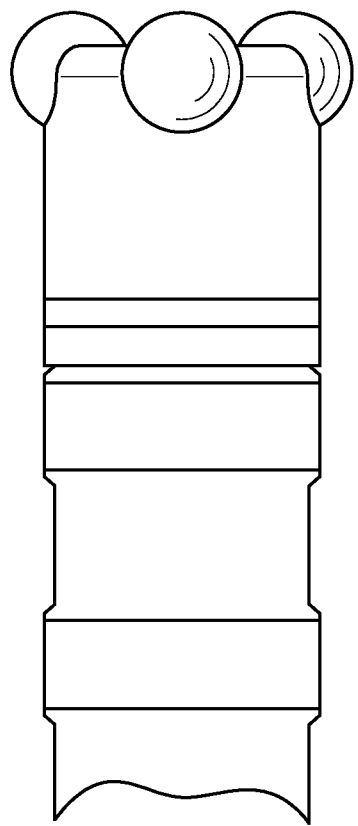
FIG. 9 is a partial side elevation view of a catheter having recessed electrodes.

A dedicated pacing electrode 32 may also be included, for synchronizing the MAP signals from the recording electrodes 20 to a local heartbeat. Physically, the reference and pacing electrodes 28 and 32 may have the shape of cylindrical bands around the longitudinal axis as depicted in FIGS. 1-3, or any other suitable shape and arrangement. If desired, each recording electrode, reference electrode, and pacing electrode may have an effective surface of substantially equivalent area. In an alternative embodiment, the pacing and reference electrodes may be recessed as shown in FIG. 9, to reduce any possibility of direct contact with tissue. In another embodiment, the reference electrode may be recessed, while the pacing electrode is larger and more likely to contact tissue.

A wire 34 or other electrical connection may be coupled with each recording electrode and to the reference electrode, for transmitting individual signals to the catheter body proximal end. Of course, electrically insulating material 26 may be positioned between each of the recording electrodes and all of the other electrodes, including ablation, reference, and pacing electrodes.

The materials of the electrodes may be selected from the group consisting of silver, silver chloride, platinum, iridium, gold, stainless steel, aluminum, and alloys and combinations thereof.

The catheter shaft is preferably both flexible and resilient, for facilitating steady contact with tissue to improve signal fidelity. The distal assembly thus facilitates contact with tissue and improves signal fidelity. Specifically, the distal section of the catheter shaft may include polymer materials having a durometer of 35D or greater flexibility.

Figure 20:
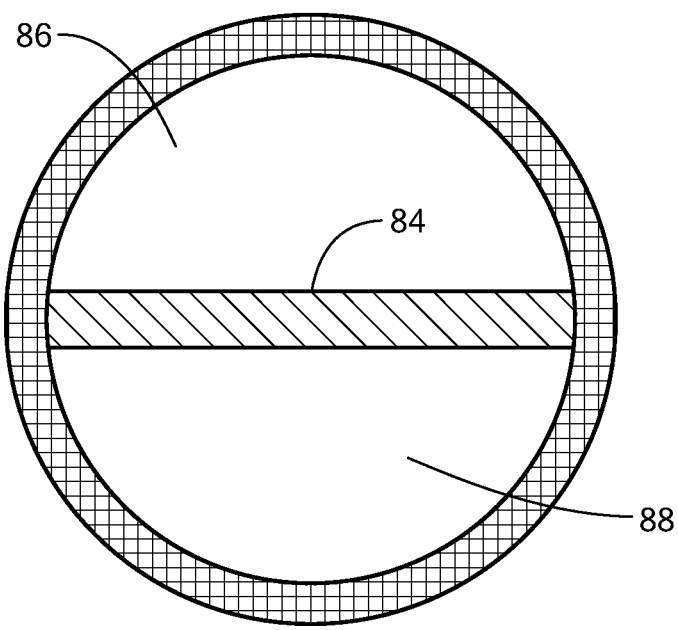
FIGS. 20-21 are transverse cross-section views of catheters, having a bending member.
Figure 21:
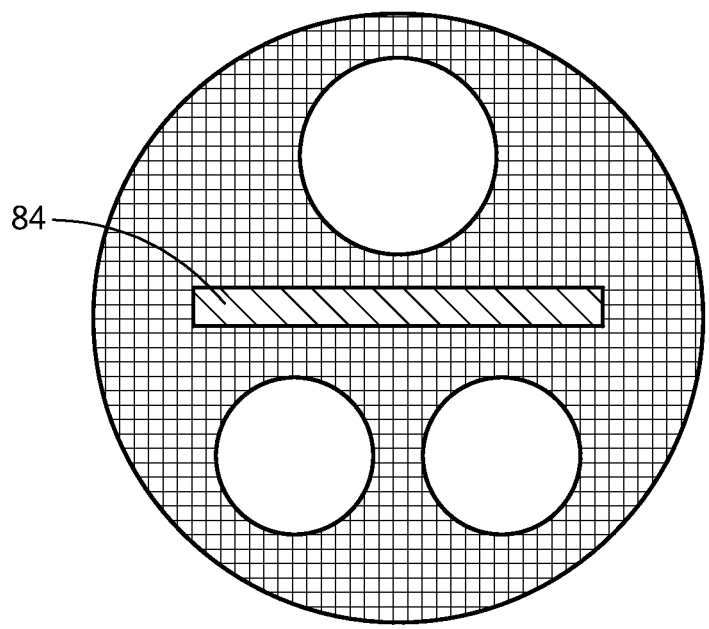

In addition, the distal section may have a thin, flexible, flat plate or bending member 84 as shown in FIGS. 20 and 21. The bending member may be made of metal, polymer or other suitable materials. Upon contact with tissue, bending member 84 will tend to cause the distal section to preferentially bend in one plane. If the recording electrodes 20 are aligned with this plane of bending, they will become preferentially oriented in stable tissue contact when the catheter tip is bent to one side or the other. The embodiment of FIG. 20 may have a lumen 86 for at least one steering or deflection pull wire and a lumen 88 for electrical wires, whereas the embodiment of FIG. 21 may have multiple lumens. In embodiments with a bending member, a steering or deflection pull wire may be anchored proximal to the bending member, rather than being attached to the distal tip.

Figure 10:
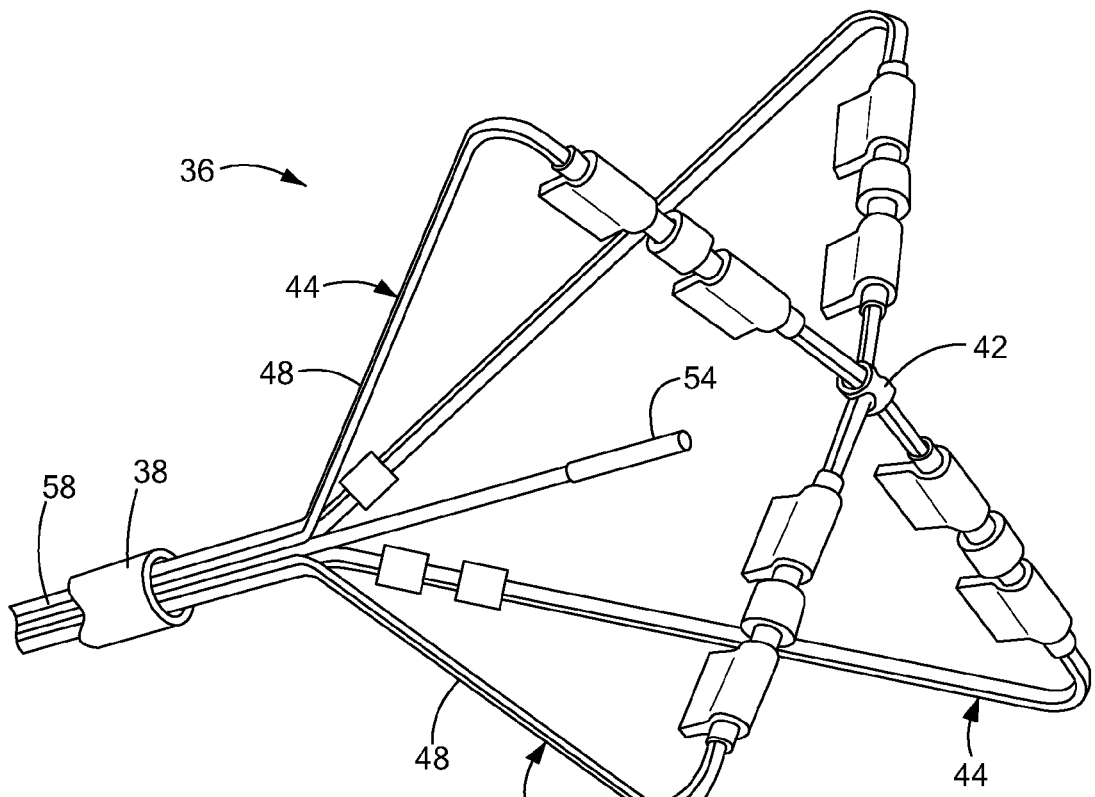
FIG. 10 is a partial external perspective view of a catheter for recording monophasic action potential electrograms, having a flexible loop array.
Figure 11:
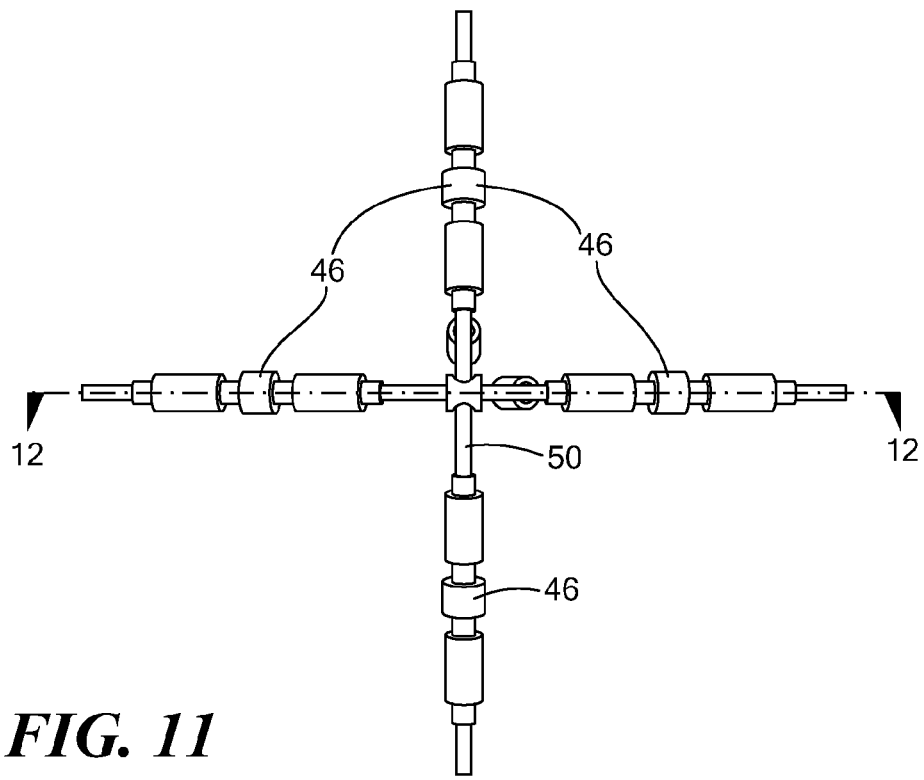
FIG. 11 is an end view of the catheter of FIG. 10.
Figure 12:
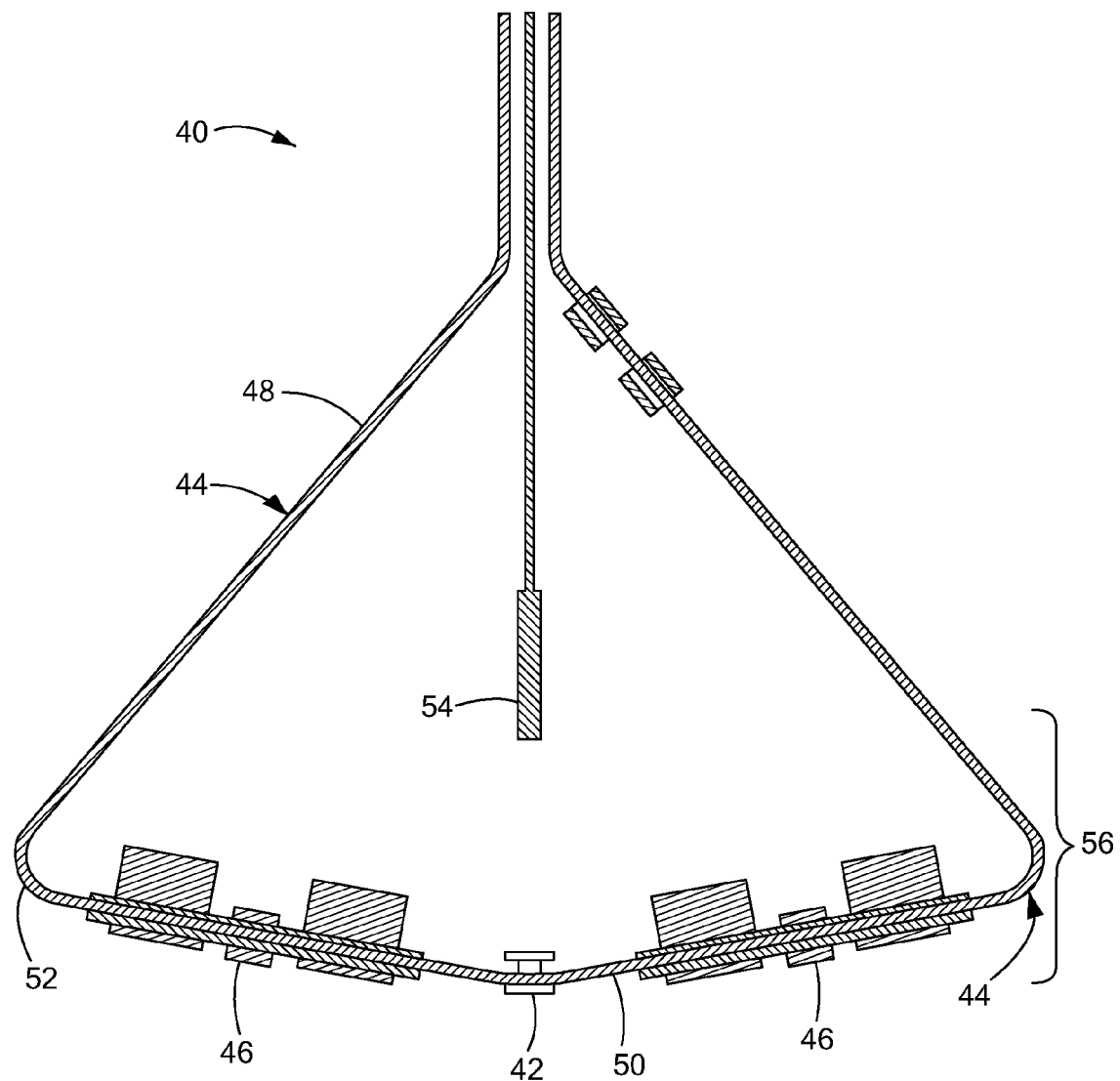
FIG. 12 is a partial longitudinal cross-section view along the line 12-12 of FIG. 11.

FIGS. 10-12 show another embodiment of the present invention, which is for example a catheter 36 for treating a patient and obtaining monophasic action potential electrograms of tissue, including a flexible catheter body 38 having proximal and distal ends defining a longitudinal axis, a distal assembly 40 affixed to the distal end of the catheter body defining a distal tip 42. The distal assembly 40 has at least three flexible and resilient loop elements 44 extending radially outward in different radial directions from positions at or near the longitudinal axis, and a MAP recording electrode 46 affixed to each loop element. Each loop element 44 having a proximal arm 48 and a distal arm 50, connected with a living hinge 52. Each of the recording electrodes 46 is affixed to an arm of a loop element 44 at a radial distance from the longitudinal axis, and each loop element 44 has at least one recording electrode 46. The recording electrodes 46 define a recording geometry, which substantially has radial symmetry around the longitudinal axis. In FIGS. 10-12, the recording geometry has a slightly conical shape. At least one reference electrode 54 may also be provided for determining reference potential, positioned a longitudinal distance 56 from the recording geometry. A wire 58 is connected to each recording electrode and to the reference electrode, for transmitting individual signals to the catheter body proximal end. The distal assembly 40 facilitates contact with tissue and improved signal fidelity.

As shown in FIGS. 10-12, the recording electrodes and ablation electrodes may be affixed to the distal arm of each loop element. In this arrangement, the distal arms of the loop elements are adapted to be pushed distally toward contact with the tissue to be treated.

In contrast, FIGS. 15-18 show another embodiment of the present invention, having a distal assembly 64 with an array of electrodes on at least three flexible and resilient loop elements 66. Each loop element 66 has a proximal arm 68 and a distal arm 70 extending radially outward from positions at or near the longitudinal axis. The proximal and distal arms 68 and 70 of each loop element 66 are connected with a living hinge 72. At least one recording electrode 74 and ablation electrode 76 are affixed to the proximal arms 68 of each loop element 66. In this arrangement, a reference electrode 78 is positioned distal of the recording geometry. Accordingly, distal assembly 64 is adapted to be pushed past distally-facing tissue to be treated, and the proximal arms 68 of the loop elements 66 are adapted to be pulled proximally toward the tissue to be treated. This embodiment facilitates treatment of the septal wall from a percutaneous access route, without the need to maneuver a distally facing electrode array approximately 180 degrees to the septal wall. Accordingly, the catheters and methods of the present invention may be used epicardially or endocardially.

Figure 13:
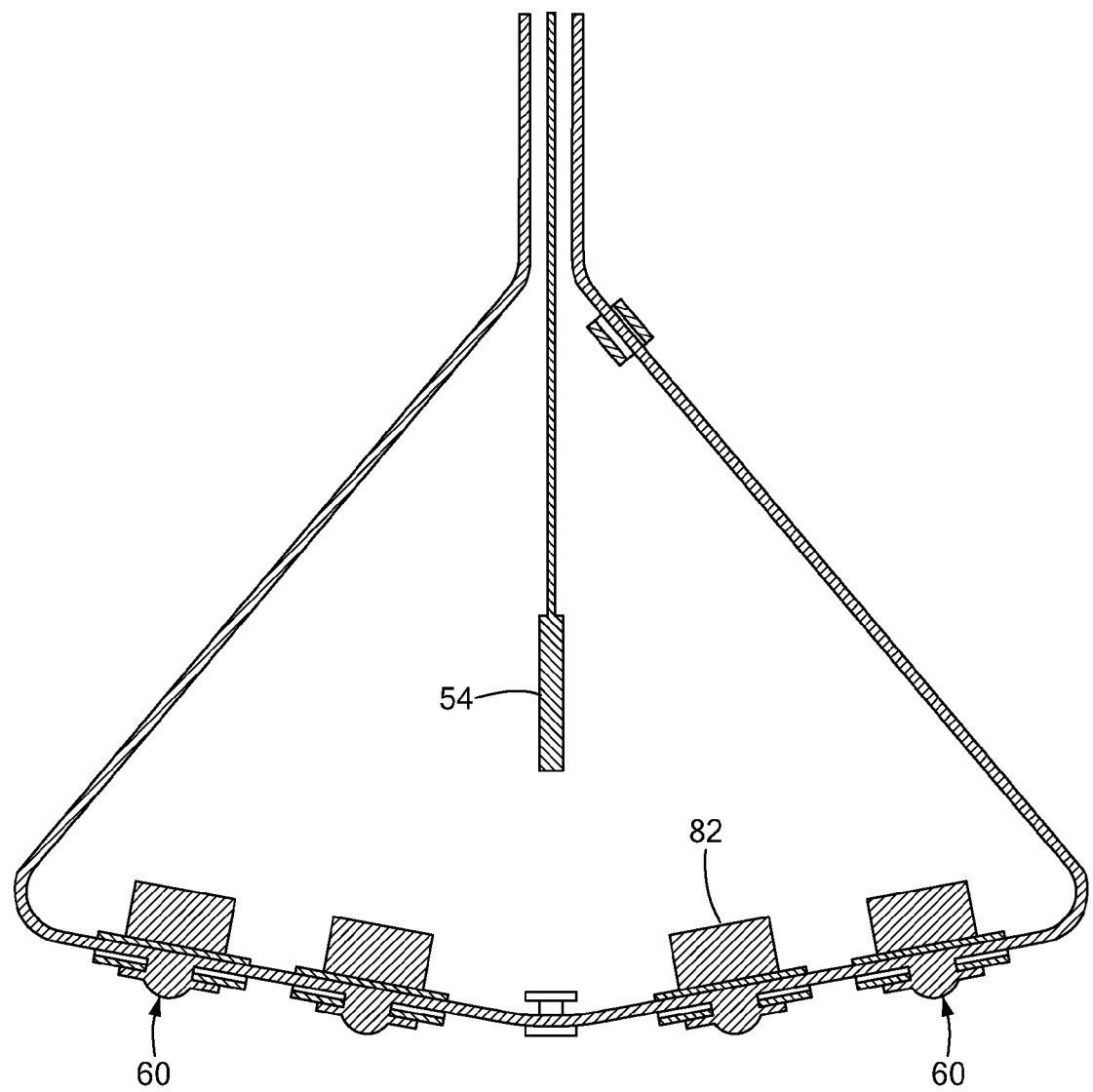
FIG. 13 is a partial longitudinal cross-section view of a catheter for recording monophasic action potential electrograms, having another flexible loop array.
Figure 14:
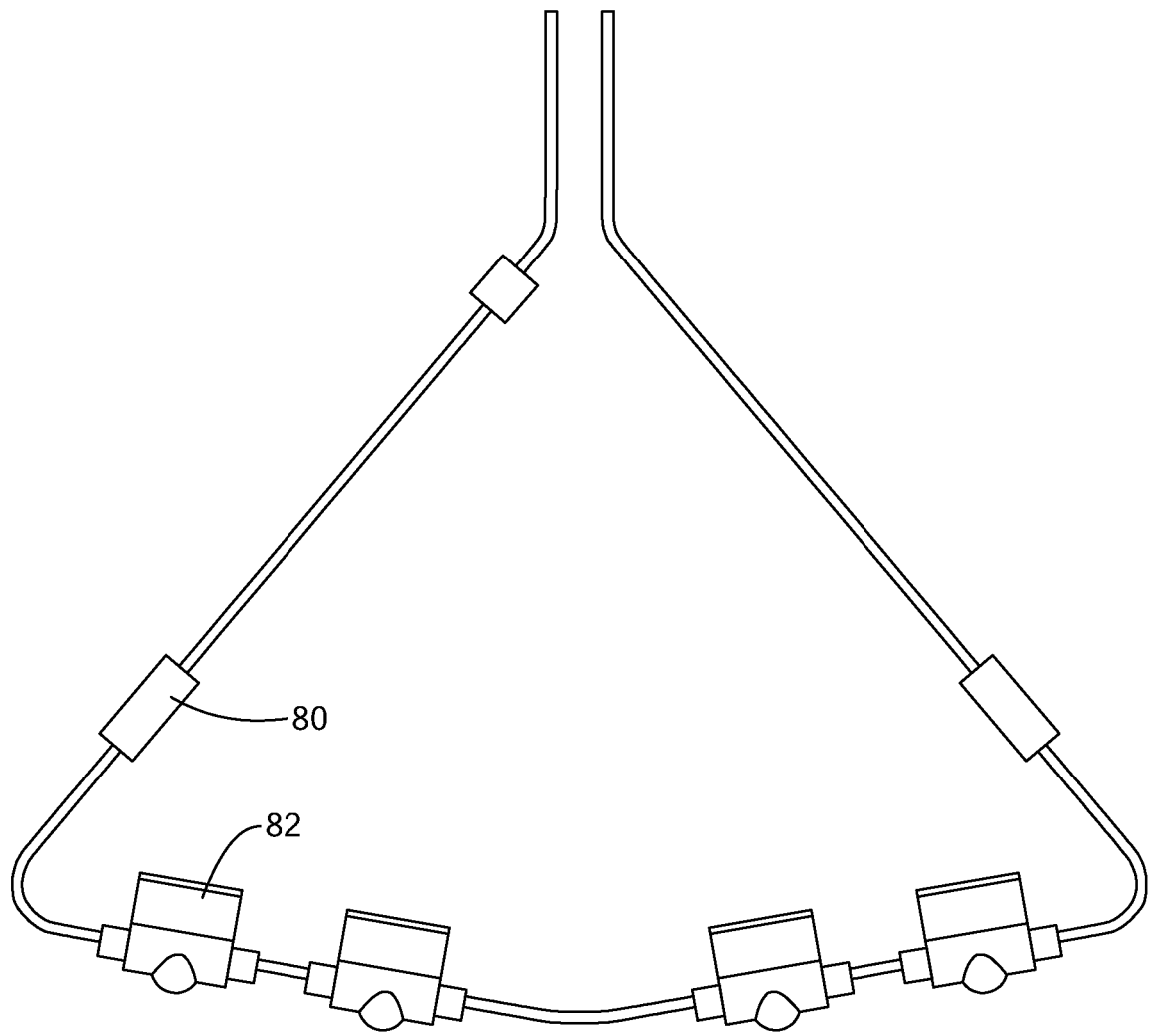
FIG. 14 is a partial side elevation view of a catheter for recording monophasic action potential electrograms, having another flexible loop array.
Figure 15:
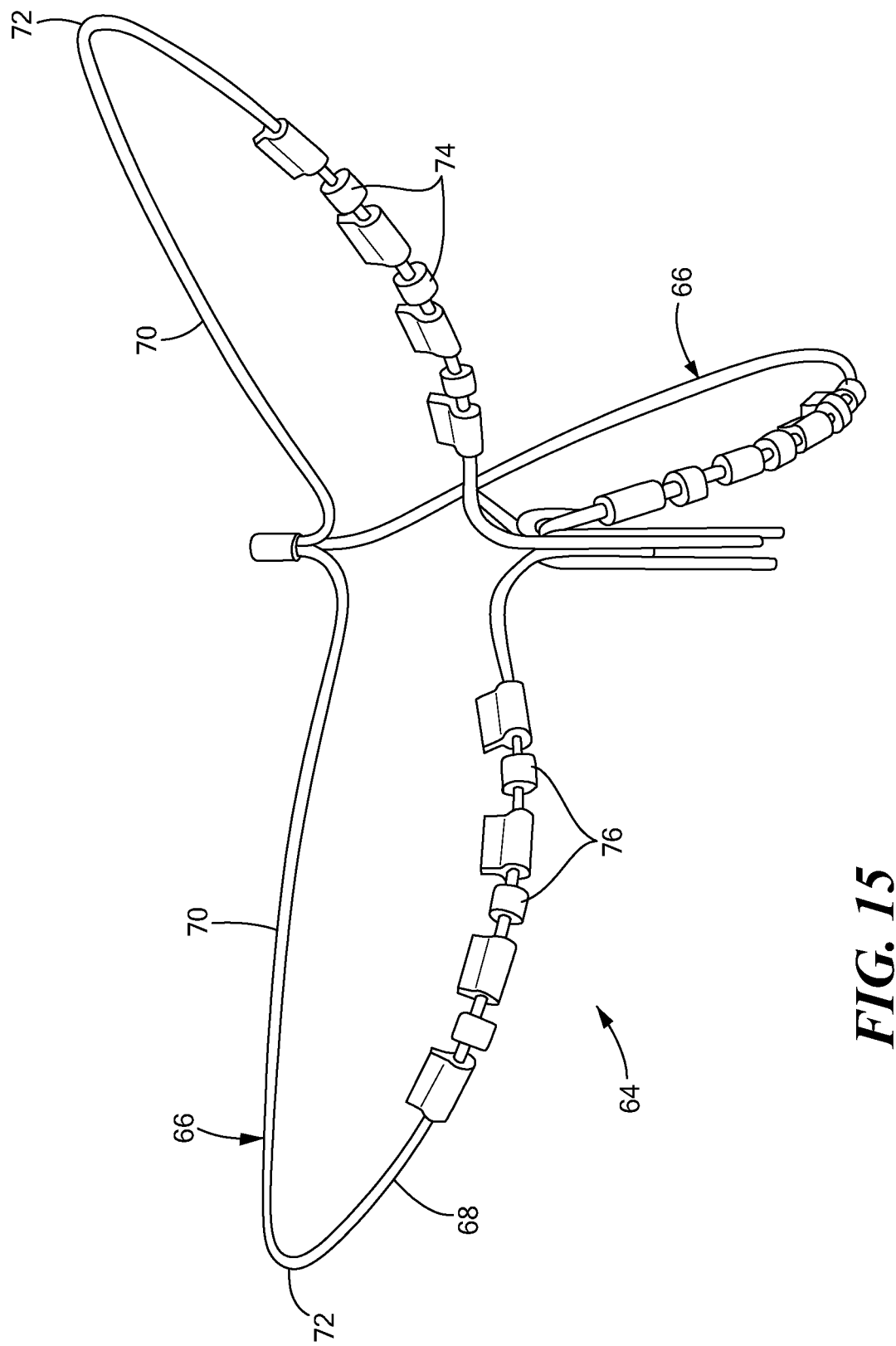
FIGS. 15-19 are external views of catheters for recording monophasic action potential electrograms, having a flexible inverse loop array.
Figure 17:
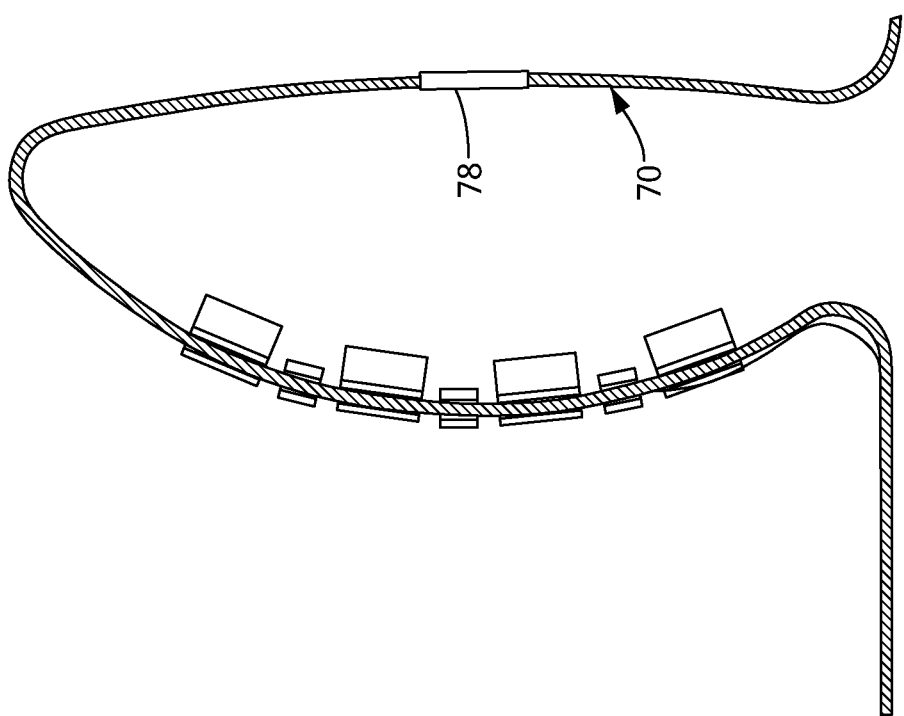
Figure 16:
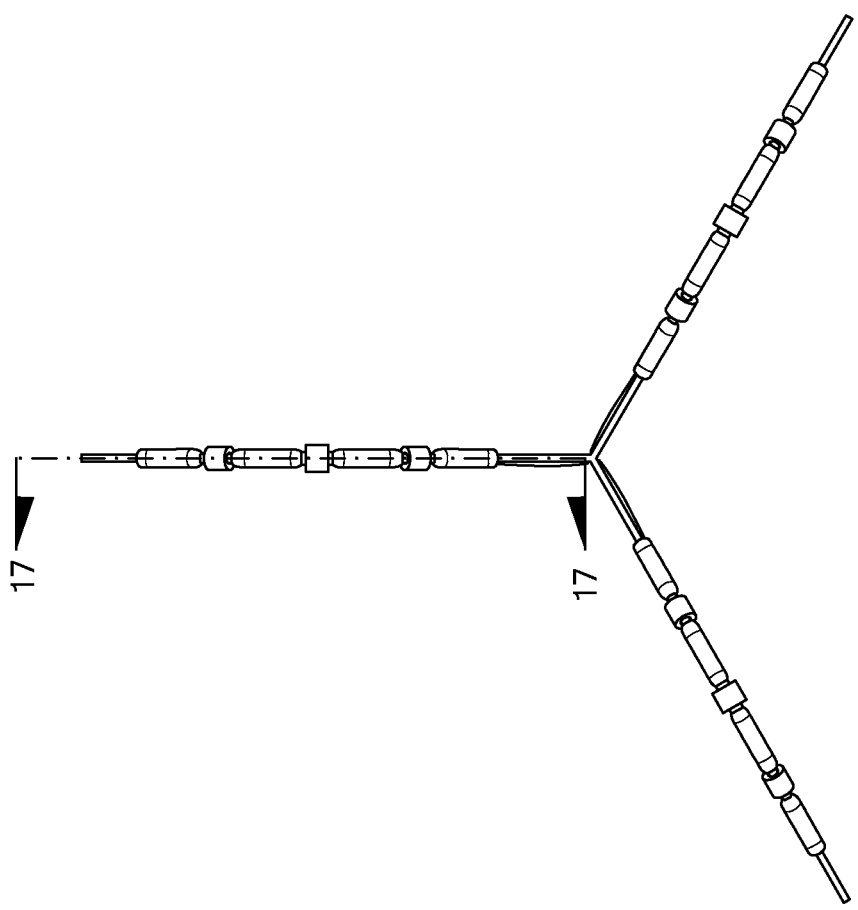
Figure 18:
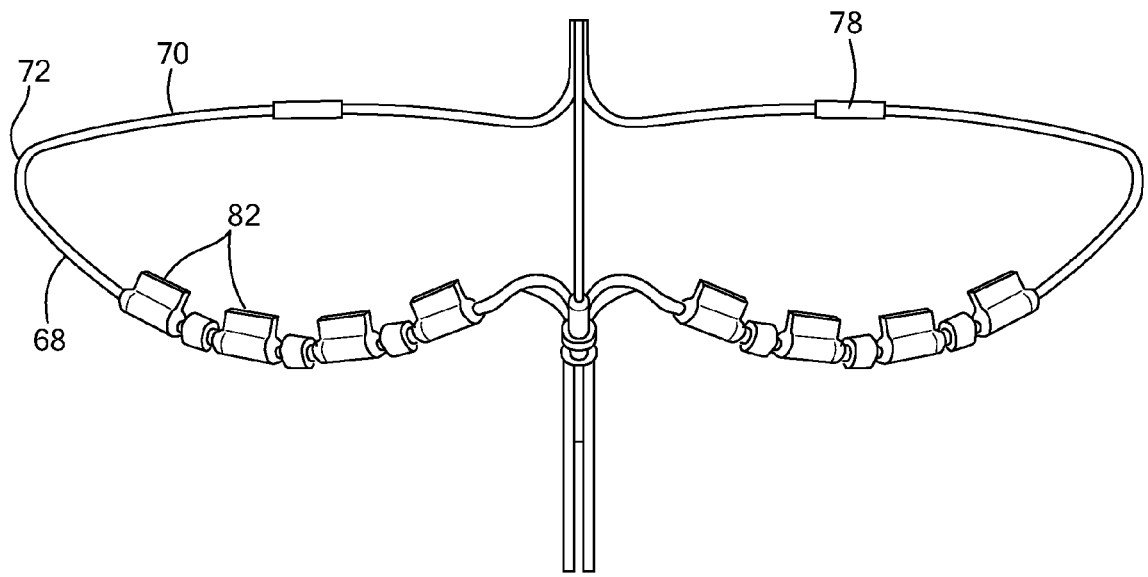
Figure 19:
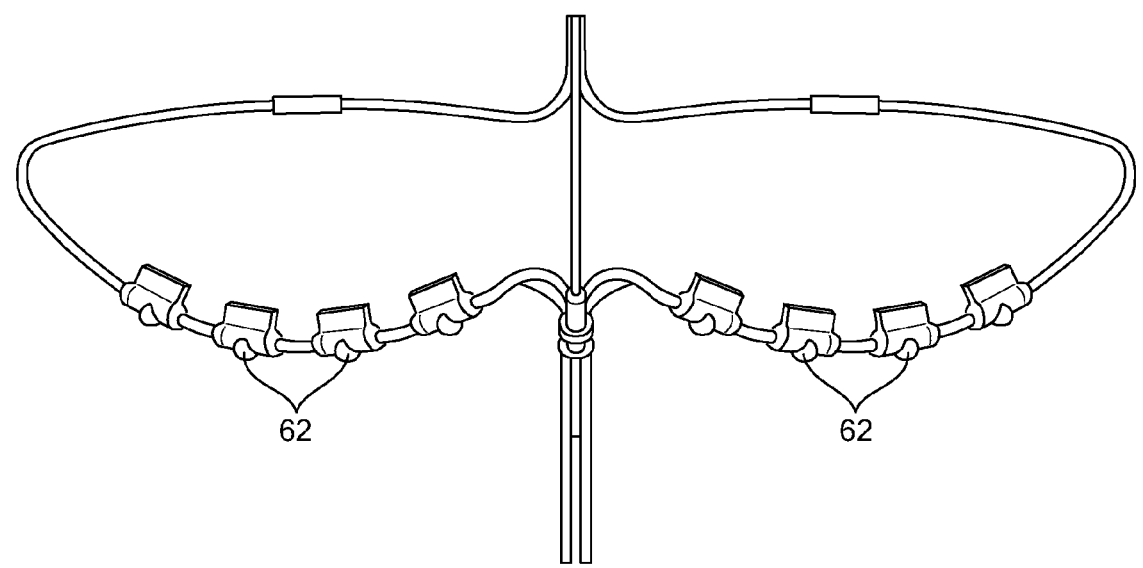

FIGS. 13 and 19 show alternate embodiments, in which the recording and ablation electrodes are combined into an array of combination electrodes 60 and 62. FIG. 14 shows another alternate embodiment, in which a reference electrode 80 is affixed to the proximal arm of a loop element rather than the catheter shaft.

As shown in FIGS. 10-19, the ablation electrodes may also have a fin 82 extending toward the other arm of its loop element, to enhance dissipation of heat from the ablation electrodes.

Methods of treating a patient according to the present invention include advancing a catheter with MAP recording electrodes along a body passage, until the recording electrodes contact tissue selected for treatment. Applying local pressure from at least one recording electrode to the tissue tends to cause local depolarization, to obtain at least one monophasic action potential signal from at least one wire connected to a recording electrode. The features of the catheters according to the present invention, including the distal assembly, facilitate good contact with the tissue and improve signal fidelity.

In addition, when more than one monophasic action potential signal is obtained, all of the signal may be displayed to the physician, or the MAP signals may be aggregated into a single display.

It should be understood that an unlimited number of configurations for the present invention could be realized. The foregoing discussion describes merely exemplary embodiments illustrating the principles of the present invention, the scope of which is recited in the following claims. In addition, unless otherwise stated, all of the accompanying drawings are not to scale. Those skilled in the art will readily recognize from the description, claims, and drawings that numerous changes and modifications can be made without departing from the spirit and scope of the invention.

What is claimed is:

1. A method of treating a patient, comprising the steps of:
advancing through the vasculature of a patient a medical device having a body portion, at least one reference electrode, and a plurality of monophasic action potential electrogram recording electrodes, the plurality of electrodes having a first collapsed configuration and a second expanded configuration, and the at least one reference electrode being located distal of the body portion and proximal of the plurality of monophasic action potential electrogram recording electrodes;
transitioning the plurality of monophasic action potential electrogram recording electrodes to the second expanded configuration, the plurality of monophasic action potential electrogram recording electrodes being a radially symmetrical distance from a longitudinal axis of the medical device in different radial directions;
positioning the plurality of monophasic action potential electrogram recording electrodes in contact with a target tissue region, the at least one reference electrode being located a distance from the target tissue region; and
obtaining at least one monophasic action potential signal from at least one recording electrode.

2. The method of claim 1, further comprising depolarizing at least a portion of the target tissue region with at least one of the plurality of electrodes.

3. The method of claim 1, further comprising obtaining a plurality of monophasic action potential signals with the plurality of electrodes.

4. The method of claim 3, further comprising aggregating the obtained monophasic action potential signals.

\* \* \* \* \*